United States Patent [19]

Kishida

[11] Patent Number: 5,556,785
[45] Date of Patent: Sep. 17, 1996

[54] LACTOBACILLUS USED TO ENHANCE IMMUNOLOGICAL FUNCTIONS

[75] Inventor: Tsunataro Kishida, Kyoto, Japan

[73] Assignees: Institut Pasteur de Kyoto, Kyoto; Shinwa Pharmaceutical Co., Ltd., Toyama; Nitto Pharmaceutical Industries Ltd., Kyoto, all of Japan

[21] Appl. No.: 141,599

[22] Filed: Oct. 27, 1993

[30] Foreign Application Priority Data

Nov. 24, 1992 [JP] Japan .................................. 4-313268

[51] Int. Cl.$^6$ .............................. C12B 1/24; C12B 1/225
[52] U.S. Cl. .................... 435/252.9; 435/855; 424/93.45
[58] Field of Search .............................. 435/252.9, 855; 424/93 J, 93.45

[56] References Cited

U.S. PATENT DOCUMENTS 4,314,995  2/1982  Hata et al. .............................. 424/93 J
4,347,240  8/1982  Mutai et al. .............................. 424/93 J

OTHER PUBLICATIONS

*ATCC Catalogue of Bacteria and Phages*, 17th ed., 1989, Rockville, Md., p. 115.

Wicken, A. J. et al., "J. Dent. Res.–Special Issue," vol. 55, 1976, pp. C34–C41.

*Primary Examiner*—Michael G. Wityshyn
*Assistant Examiner*—Kristin Larson
*Attorney, Agent, or Firm*—Wenderoth, Lind & Ponack

[57] ABSTRACT

A composition containing powdered *Lactobacillus brevis* subsp. *coagulans* is used to enhance the immunological functions of a patient, particularly with respect to increasing interferon production, 2-5A synthetase activity and Natural Killer activity.

7 Claims, No Drawings

LACTOBACILLUS USED TO ENHANCE IMMUNOLOGICAL FUNCTIONS

BACKGROUND OF THE INVENTION

The present invention relates to an enhancer of immunological functions which increases human interferon production and enhances human immunological functions.

Interferon (IFN) is produced in cells, such as leucocytes, fibroblasts and T-lymphocytes, which are infected with virus, and it protects other cells from virus infections. Thus, the interferon has an inhibitory effect on multiplication of virus.

Of the IFNs, IFN-α production has been reported to decrease in patients with cancer, diabetes, tuberculosis, etc., and the ability of IFN-α production is inversely related to the susceptibility to infection.

Further, it has also been reported that IFN-γ production is decreased in patients with cancer, and increased in Hashimoto's disease, an autoimmune disease.

It is also known that IFN-γ production contributes to human immune functions which differ from those reflected by IFN-α production.

Thus, the capacity of IFN-α and IFN-γ production is considered to be a useful parameter of evaluating immunological functions of individual.

It is thought that the enhancement of these immunological functions might improve the general condition and the quality of life of patients with impaired immunological function.

In order to enhance the immunological functions, it has been proposed to administer IFN or to utilize a strong immunopotentiator such as OK432.

There is a known correlation between Natural Killer(NK) activity and the condition of cancer patients, and it is well-known that IFN administration enhances the activity.

However, repeated use of IFN or an immunopotentiator like OK432 has been found to cause side-effects, such as an imbalance of homeostasis, pyrexia and malaise.

Therefore, instead of administering IFN, enhancers of immunological functions (IFN inducers) have been developed which increase interferon production in a human body and enhance immunological functions. In fact, double helix RNA, pyran copolymer, anionic high polymer, and kinds of polysaccharides (see Japanese Patent Publication No. Hei. 3-9882) have been already proposed as enhancers of immunological functions.

However, since these well-known enhancers of immunological functions do not naturally exist in the human body, these enhancers have some toxicities, which might cause side-effects in the human body when used in the treatment of infections or tumors.

SUMMARY OF THE INVENTION

An object of the present invention is to provide an enhancer of immunological functions which increases interferon production to enhance human immunological functions. By using the enhancer of immunological functions, infections and tumors may be cured or prevented.

In this point, the present inventors have discovered an enhancer of immunological functions comprising powdered *Lactobacillus brevis* subsp. *coagulans*. This microorganism has been deposited at the National Institute of Bioscience and Human-Technology, 1-3, Higashi 1-chome, Tsukuba-shi, Ibaraki-ken, Japan on Jun. 8, 1994 and bears accession No. Ferm BP-4693.

The powdered *Lactobacillus brevis* subsp. *coagulans* may be produced, for instance, using the following procedure:

First, a mold starter as the Lactobacillus source is agitated and cultured for 18–40 hours at 25–35° C. and at 100 rpm in a culture medium such as culture medium A, B or C described in the following paragraph.

After this, the culture solution is concentrated or centrifuged and then lyophilized into powdered *Lactobacillus brevis* subsp. *coagulans*.

| Culture Medium A | |
| --- | --- |
| ① yeast extract | 0.5 % |
| ② glucose | 1.5% |
| ③ potassium dihydrogenphosphate | 0.5% |
| ④ sodium hydrogenphosphate | 2.0% |
| ⑤ sodium chloride | 0.425% |
| ⑥ sodium hydroxide | 0.0375% |
| ⑦ defatted soybean extract | 8.75% |
| ⑧ precipitated calcium carbonate | 0.1% |
| Culture Medium B | |
| polypeptone | 0.5~1.0% |
| yeast extract | 0.5~1.0% |
| glucose | 0.5~1.0% |
| pH | 6.5~7.0 |
| Culture medium C | |
| yeast extract | 0.55% |
| 3 | |
| glucose | 1.10% |
| polypeptone | 1.25% |
| sodium dihydrogenphosphate | 0.025% |
| sodium hydrogenphosphate | 0.025% |
| magnesium sulfate | 0.01% |
| magnanese sulfate | 0.0005% |
| pH | 6.5~7.0 |

In preparing the culture medium A, the components ①–⑦ are dissolved under heating in water. Then, after the component ⑧ is added to the solution, the solution is adjusted to have a pH of 6.8–7.0, and then is sterilized for 15 minutes with a high-pressure steam at 121° C. In addition, the defatted soy bean extract⑦ is prepared using the following procedure:

After defatted soy beans are soaked in diluted hydrochloric acid (about 0.25 N), pepsin was added, and the mixture is kept at 37° C. for 40–48 hours with occasional stirring and digested. After being digested, sodium hydroxide is added to neutralize the solution. Then the solution is centrifuged and the supernatant is taken as the defatted soy bean extract.

It is desirable to obtain a mold starter from food, such as vegetables fermented by Lactobacillus (Tsukemono). 50 l of each culture media A, B and C produces 100–500 g of powdered bacteria, wherein 2–50 billion of bacteria is comprised per 1 g ($2 \times 10^9$–$5 \times 10^{10}$/g).

It is desirable to administer the powdered bacteria orally in the form of a powder, tablet, capsule, or granulated powder.

In making the tablets, powdered bacteria may be blended with L-sodium glutamic acid (10%), or with a mixture of skim milk powder (10%) and L-sodium glutamic acid (1%) as a dispersion medium, and dried potato starch as an excipient.

DETAILED DESCRIPTION OF THE PREFERRED EMBODIMENT

The preferred embodiment of the present invention is described in detail hereinbelow.

A mold starter is acquired from *Brassica japonica* var. Suigukina fermented by Lactobacillus. The mold starter is agitated in culture medium A for 30 hours at 25° C.–35° C. and at 100 rpm to culture the bacteria. Then, the culture solution is centrifuged at about 10000 rpm and lyophilized into powdered bacteria, which is named *Lactobacillus brevis* PK.

The powdered bacteria acquired in this method possesses the following features (1)–(6) which are characteristics of Lactobacillus, and the powdered bacteria is also identified as *Lactobacillus brevis* subsp. *coagulans* based on its glycolysis characteristics as shown in Table 1 below.

(1) It is a Gram positive rod.

(2) It dissolves calcium carbonate in a medium.

(3) It produces lactic acid from glucose in a medium.

(4) Ability of reducing nitrate is negative.

(5) Ability of liquefying gelatin is negative.

(6) Ability of digesting casein is negative.

Next, powdered dried potato is added to the powdered bacteria acquired in the above procedure and the powdered bacteria is adjusted to have $10^8$–$10^9$ bacteria per 1 g. Further, lactose anhydrous as an excipient is added. Thereby, tablets of 250 mg are made.

Six tablets per day ($3 \times 10^8$ bacteria) were administered orally to 4 healthy human males and 6 healthy human females, aged 25 to 65 years, for 4 weeks. Peripheral blood was drawn in heparin tubes before administration and after 2 and 4 weeks. IFN-α and IFN-γ production, Natural Killer (NK) activity and 2–5A (2', 5' oligoadenylic acid) synthetase activity were measured and the result of the measurement was shown in Tables 2 and 3.

IFNα and -γ were measured by bio-assay methods with 50% CPE (cytopathic effect) using FL-cell (human amion origin) and Sindobis virus.

An example of the method used for measuring IFN-α is described as follows:

Heparinized peripheral blood was treated for IFN production by the whole blood method. After that, 2 ml of whole blood was collected in a centrifuge tube. HVJ(Sendai virus) was added at a final concentration of 500 HA/ml. It was cultured for 20 hrs at 37° C. and then centrifuged at 3,000 rpm. Supernatants were harvested for the measurement of IFN-α production.

An example of the method used for measuring IFN-γ is described as follows:

Heparinized peripheral blood was diluted 4 times in Eagle's MEM, and PHA-P (purchased from Sigma) was added to give 25 μg /ml concentration After 48 hrs of culture at 37° C., it was centrifuged at 3,000 rpm and the supernatants were harvested as IFN-γ samples.

In measuring NK activity, peripheral mononuclear cells were isolated from peripheral blood by the Ficoll-plaque method, and effector cells were obtained. K562 cells labeled with $Cr^{51}$ as target cells were mixed with the effector cells in an E/T ratio of 20:1. Cytotoxicity was measured by the conventional method.

As 2–5A synthetase activity from non-stimulated plasma was too low to measure, that of stimulated plasma with HVJ (Sendai virus) for 20 hrs were measured for the evaluation of IFN-α production capacity. Radioimmunoassay kit (produced by Eiken Chemical Co., Tokyo) was used for measuring 2', 5'-oligo adenylate (2–5A) synthetase activity.

From the results shown in Table 2 and Table 3, it was clear that the powdered bacteria prepared by the above procedure increased IFN-α production, NK activity and 2–5A synthetase activity.

Further, after administration of the powdered bacteria, blood tests revealed no major deviation from the standard values in any individual.

TABLE 1

|  | test 1 | test 2 |  | test 1 | test 2 |
|---|---|---|---|---|---|
| Arabinose | + | + | Cellobiose | – | – |
| Xylose | + | + | Lactose | – | – |
| Rhamnose | – | – | Trehalose | – | – |
| Sorbose | – | – | Melibiose | ± | + |
| Ribose | ± | + | Raffinose | – | – |
| Glucose | + | + | Melezitose | – | – |
| gas | + | + | Starch pH | – | – |
| Mannose | – | – | Mannitol | – | – |
| Fructose | + | + | Sorbitol | – | – |
| Galactose | + | + | Esculin pH | – | – |
| Sucrose | – | – | Salicin | – | – |
| Maltose | + | + | Amygdalin | – | – |

TABLE 2

|  | IFNα production IU/ml | | | IFNγ production IU/ml | | |
|---|---|---|---|---|---|---|
|  | 0 | 2W later | 4W later | 0 | 2W later | 4W later |
| female 1 | 5518 | 9545 | 9884 | 84 | 145 | 358 |
|  | 100.0 | 173.0 | 179.1 | 100.0 | 172.6 | 426.2 |
| female 2 | 6457 | 10784 | 21986 | 323 | 338 | 705 |
|  | 100.0 | 167.0 | 340.5 | 100.0 | 104.6 | 218.3 |
| female 3 | 5254 | 15073 | 10584 | 424 | 402 | 353 |
|  | 100.0 | 286.9 | 201.4 | 100.0 | 94.8 | 83.3 |
| female 4 | 7243 | 4162 | 5712 | 243 | 185 | 309 |
|  | 100.0 | 57.5 | 78.9 | 100.0 | 76.1 | 127.2 |
| male 1 | 5208 | 5511 | 6141 | 506 | 960 | 270 |
|  | 100.0 | 105.8 | 117.9 | 100.0 | 189.7 | 53.4 |
| male 2 | 7240 | 12693 | 9999 | 234 | 110 | 110 |
|  | 100.0 | 175.3 | 138.1 | 100.0 | 47.0 | 41.0 |
| male 3 | 6495 | 7229 | 10617 | 69 | 60 | 137 |
|  | 100.0 | 111.3 | 163.5 | 100.0 | 87.0 | 198.6 |
| female 5 | 4418 | 9083 | 4416 | 75 | 31 | 62 |
|  | 100.0 | 205.6 | 100.0 | 100.0 | 41.3 | 82.7 |
| female 6 | 3168 | 7345 | 10320 | 32 | 87 | 98 |
|  | 100.0 | 231.8 | 325.8 | 100.0 | 271.2 | 306.3 |
| male 4 | 11620 | 22075 | 9939 | 126 | 12 | 41 |
|  | 100.0 | 190.0 | 85.5 | 100.0 | 9.5 | 32.5 |
| average | 6262.1 | 10350 | 9959.8 | 211.6 | 233 | 244.3 |
|  | 100.0 | 165.3 | 159.0 | 100.0 | 110.1 | 112.8 |

TABLE 3

|  | NK activity % | | | 2–5 A activity pmol/ml | | |
|---|---|---|---|---|---|---|
|  | 0 | 2W later | 4W later | 0 | 2W later | 4W later |
| female 1 | 26 | 50 | 47 | 29.4 | 32.0 | 22.1 |
|  | 100.0 | 192.3 | 180.8 | 100.0 | 108.8 | 75.2 |
| female 2 | 43 | 62 | 59 | 49.3 | 41.5 | 45.9 |
|  | 100.0 | 144.2 | 137.2 | 100.0 | 84.2 | 93.1 |
| female 3 | 42 | 33 | 42 | 10.0 | 61.0 | 45.2 |
|  | 100.0 | 78.6 | 100.0 | 100.0 | 610.0 | 452.0 |
| female 4 | 42 | 51 | 51 | 10.0 | 22.6 | 66.3 |
|  | 100.0 | 121.4 | 121.4 | 100.0 | 226.0 | 663.0 |
| male 1 | 24 | 30 | 31 | 22.8 | 48.4 | 45.0 |
|  | 100.0 | 125.0 | 129.2 | 100.0 | 212.3 | 197.4 |
| male 2 | 33 | 89 | 36 | 84.9 | 102.5 | 119.8 |
|  | 100.0 | 269.7 | 109.1 | 100.0 | 120.7 | 141.1 |
| male 3 | 53 | 62 | 63 | 47.5 | 61.8 | 103.2 |
|  | 100.0 | 117.0 | 118.9 | 100.0 | 130.1 | 217.3 |
| female 5 | 36 | 44 | 62 | 54.8 | 323.5 | 792.4 |
|  | 100.0 | 122.2 | 172.2 | 100.0 | 590.3 | 1446.0 |
| female 6 | 42 | 79 | 53 | 45.0 | 53.1 | 118.9 |
|  | 100.0 | 188.1 | 126.2 | 100.0 | 118.0 | 264.2 |
| male 4 | 54 | 79 | 63 | 84.0 | 99.8 | 108.7 |
|  | 100.0 | 146.3 | 116.7 | 100.0 | 118.8 | 264.2 |

TABLE 3-continued

|  | NK activity % | | | 2-5 A activity pmol/ml | | |
| --- | --- | --- | --- | --- | --- | --- |
|  | 0 | 2W later | 4W later | 0 | 2W later | 4W later |
| average | 39.5 | 57.9 | 50.7 | 43.8 | 58.1 | 75.0 |
|  | 100.0 | 146.6 | 128.4 | 100.0 | 132.6 | 171.2 |

What is claimed is:

1. A composition comprising powdered *Lactobacillus brevis* subsp. *coagulans* FERM BP-4693.

2. The composition of claim 1, wherein said powdered *Lactobacillus brevis* subsp. *coagulans* comprises $2 \times 10^9 - 5 \times 10^{10}$ of bacteria per 1 g.

3. The composition of claim 1, in the form of a tablet, capsule or granule.

4. The composition of claim 2, in the form of a tablet, capsule or granule.

5. The composition of claim 1, wherein the *Lactobacillus brevis* subsp. *coagulans* is obtained from *Brassica japonica* var. Suigukina.

6. The composition of claim 2, wherein the *Lactobacillus brevis* subsp. *coagulans* is obtained from *Brassica japonica* var. Suigukina.

7. The composition of claim 3, wherein the *Lactobacillus brevis* subsp. *coagulans* is obtained from *Brassica japonica* var. Suigukina.

* * * * *